(12) United States Patent  (10) Patent No.: US 7,713,218 B2
Babaev et al.  (45) Date of Patent: *May 11, 2010

(54) REMOVABLE APPLICATOR NOZZLE FOR ULTRASOUND WOUND THERAPY DEVICE

(75) Inventors: Eilaz Babaev, Minnetonka, MN (US); Michael T. Peterson, Lakeville, MN (US); Alan Van Houten, Carver, MN (US); Greg Doten, Minneapolis, MN (US)

(73) Assignee: Celleration, Inc., Eden Prairie, MN (US)

( * ) Notice: Subject to any disclaimer, the term of this patent is extended or adjusted under 35 U.S.C. 154(b) by 1044 days.

This patent is subject to a terminal disclaimer.

(21) Appl. No.: 11/168,620

(22) Filed: Jun. 27, 2005
(Under 37 CFR 1.47)

(65) Prior Publication Data

US 2007/0016110 A1  Jan. 18, 2007

Related U.S. Application Data

(60) Provisional application No. 60/693,560, filed on Jun. 23, 2005.

(51) Int. Cl.
*A61H 1/00* (2006.01)

(52) U.S. Cl. .......................... 601/2; 600/439

(58) Field of Classification Search .............. 222/4, 222/5, 80, 81, 165, 167, 181.2, 594, 598, 222/617; 251/208; 600/407, 408, 439; 601/2–4; 604/20–22
See application file for complete search history.

(56) References Cited

U.S. PATENT DOCUMENTS 2,534,046 A  12/1950  Mau
(Continued)

FOREIGN PATENT DOCUMENTS

EP  0 156 4009 A2  2/1985
(Continued)

OTHER PUBLICATIONS

Ennis et al., Ostomy/Wound Management 51(8):24-39 (2005).
(Continued)

*Primary Examiner*—Long V Le
*Assistant Examiner*—Saurel J Selkin
(74) *Attorney, Agent, or Firm*—Patterson, Thuente, Skaar & Christensen, P.A.

(57) ABSTRACT

A removable applicator nozzle for use in treating a wound is provided. The removable applicator nozzle includes a nozzle, a valve and a cup. The nozzle includes a proximal portion, a distal opening and a valve interface. The proximal portion of the nozzle is engagable with a portion of a transducer of an ultrasound wound therapy device. The distal opening of the nozzle allows at least a portion of a tip of the transducer to pass therethrough. The valve is engagable with the valve interface of the nozzle and the valve selectively allows fluid to flow therethrough. The cup includes an aperture and a puncturing device. The aperture is engagable with the valve and the puncturing device is able to puncture a bottle that is inserted on the cup. Fluid flows from the bottle, through the aperture and the valve and onto a tip of the transducer. The fluid is then moved to the distal opening of the nozzle by a vacuum effect.

17 Claims, 6 Drawing Sheets

U.S. PATENT DOCUMENTS

| | | |
|---|---|---|
| 2,889,852 A | 6/1959 | Dunlap |
| 3,207,181 A | 9/1965 | Elizabeth |
| 3,243,122 A | 3/1966 | Snaper |
| 3,275,059 A | 9/1966 | McCullough |
| 3,392,916 A | 7/1968 | Engstrom et al. |
| 3,504,887 A | 4/1970 | Okerblom |
| 3,561,444 A | 2/1971 | Boucher |
| 3,685,694 A * | 8/1972 | Ianelli .................... 222/82 |
| 3,765,606 A | 10/1973 | Moss et al. |
| 3,860,173 A | 1/1975 | Sata |
| 3,952,918 A * | 4/1976 | Poitras et al. .............. 222/82 |
| 4,052,004 A | 10/1977 | Martin et al. |
| 4,085,893 A | 4/1978 | Durley, III |
| 4,153,201 A | 5/1979 | Berger et al. |
| 4,251,031 A | 2/1981 | Martin et al. |
| 4,271,705 A | 6/1981 | Crostack |
| 4,294,407 A | 10/1981 | Reichl et al. |
| 4,301,093 A | 11/1981 | Eck et al. |
| 4,301,968 A | 11/1981 | Berger et al. |
| 4,309,989 A | 1/1982 | Fahim |
| 4,319,155 A | 3/1982 | Nakai et al. |
| 4,334,531 A | 6/1982 | Reichl et al. |
| 4,352,459 A | 10/1982 | Berger et al. |
| 4,414,202 A | 11/1983 | Silvetti |
| 4,428,531 A | 1/1984 | Martin |
| 4,466,571 A | 8/1984 | Muhlbauer |
| 4,530,360 A | 7/1985 | Duarte |
| 4,541,564 A | 9/1985 | Berger et al. |
| 4,582,149 A | 4/1986 | Slaughter, Jr. |
| 4,582,654 A | 4/1986 | Karnicky et al. |
| 4,619,400 A | 10/1986 | Van der Burgt |
| 4,642,581 A | 2/1987 | Erickson |
| 4,655,393 A | 4/1987 | Berger |
| 4,659,014 A | 4/1987 | Soth et al. |
| 4,679,551 A | 7/1987 | Anthony |
| 4,726,523 A | 2/1988 | Kokubo et al. |
| 4,726,525 A | 2/1988 | Yonekawa et al. |
| 4,733,820 A | 3/1988 | Endo et al. |
| 4,756,478 A | 7/1988 | Endo et al. |
| 4,783,003 A | 11/1988 | Hirabayashi et al. |
| 4,790,479 A | 12/1988 | Matsumoto et al. |
| 4,793,339 A | 12/1988 | Matsumoto et al. |
| 4,818,697 A | 4/1989 | Liboff et al. |
| 4,850,534 A | 7/1989 | Takahashi et al. |
| 4,877,989 A | 10/1989 | Drews et al. |
| 4,905,671 A | 3/1990 | Senge et al. |
| 4,930,700 A | 6/1990 | McKown |
| 4,941,614 A * | 7/1990 | Ilott ...................... 239/294 |
| 4,941,618 A | 7/1990 | Hildebrand et al. |
| 4,961,885 A | 10/1990 | Avrahami et al. |
| 4,982,730 A | 1/1991 | Lewis, Jr. |
| 5,002,059 A | 3/1991 | Crowley et al. |
| 5,013,241 A | 5/1991 | von Gutfeld et al. |
| 5,040,537 A | 8/1991 | Katakura |
| 5,063,922 A | 11/1991 | Hakkinen |
| 5,076,266 A | 12/1991 | Babaev |
| 5,104,042 A | 4/1992 | McKown |
| 5,115,805 A | 5/1992 | Bommannan et al. |
| 5,134,993 A | 8/1992 | van der Linden et al. |
| 5,143,588 A | 9/1992 | Liboff et al. |
| 5,163,433 A | 11/1992 | Kagawa et al. |
| 5,172,692 A | 12/1992 | Kulow et al. |
| 5,186,162 A | 2/1993 | Talish et al. |
| 5,197,946 A | 3/1993 | Tachibana |
| 5,211,160 A | 5/1993 | Talish et al. |
| 5,231,975 A | 8/1993 | Bommannan et al. |
| 5,259,384 A | 11/1993 | Kaufman et al. |
| 5,269,291 A | 12/1993 | Carter |
| 5,309,898 A | 5/1994 | Kaufman et al. |
| 5,315,998 A | 5/1994 | Tachibana et al. |
| 5,316,000 A | 5/1994 | Chapelon et al. |
| 5,318,014 A | 6/1994 | Carter |
| 5,323,769 A | 6/1994 | Bommannan et al. |
| 5,324,255 A | 6/1994 | Passafaro et al. |
| 5,345,940 A | 9/1994 | Seward et al. |
| 5,347,998 A | 9/1994 | Hodson et al. |
| 5,362,309 A | 11/1994 | Carter |
| 5,374,266 A | 12/1994 | Kataoka et al. |
| 5,380,411 A | 1/1995 | Schlief |
| 5,393,296 A | 2/1995 | Rattner |
| 5,437,606 A | 8/1995 | Tsukamoto |
| 5,515,841 A | 5/1996 | Robertson et al. |
| 5,515,842 A | 5/1996 | Ramseyer et al. |
| 5,516,043 A | 5/1996 | Manna et al. |
| 5,520,166 A | 5/1996 | Ritson et al. |
| 5,520,612 A | 5/1996 | Winder et al. |
| 5,527,350 A | 6/1996 | Grove et al. |
| 5,529,572 A | 6/1996 | Spector |
| 5,545,124 A | 8/1996 | Krause et al. |
| 5,547,459 A | 8/1996 | Kaufman et al. |
| 5,551,416 A | 9/1996 | Stimpson et al. |
| 5,554,172 A | 9/1996 | Horner et al. |
| 5,556,372 A | 9/1996 | Talish et al. |
| 5,573,497 A | 11/1996 | Chapelon |
| 5,616,140 A | 4/1997 | Prescott |
| 5,618,275 A | 4/1997 | Bock |
| 5,626,554 A | 5/1997 | Ryaby et al. |
| 5,643,179 A | 7/1997 | Fujimoto |
| 5,656,016 A | 8/1997 | Ogden |
| 5,658,323 A | 8/1997 | Miller |
| 5,688,224 A | 11/1997 | Forkey et al. |
| 5,699,805 A | 12/1997 | Seward et al. |
| 5,707,402 A | 1/1998 | Heim |
| 5,707,403 A | 1/1998 | Grove et al. |
| 5,730,705 A | 3/1998 | Talish et al. |
| 5,735,811 A | 4/1998 | Brisken |
| 5,743,863 A | 4/1998 | Chapelon |
| 5,752,924 A | 5/1998 | Kaufman et al. |
| 5,762,616 A | 6/1998 | Talish |
| 5,785,972 A | 7/1998 | Tyler |
| 5,835,678 A | 11/1998 | Li et al. |
| 5,843,139 A | 12/1998 | Goedeke et al. |
| 5,879,314 A | 3/1999 | Peterson et al. |
| 5,879,364 A | 3/1999 | Bromfield et al. |
| 5,882,302 A | 3/1999 | Driscoll, Jr. et al. |
| 5,894,841 A | 4/1999 | Voges |
| 5,904,659 A | 5/1999 | Duarte et al. |
| 5,947,921 A | 9/1999 | Johnson et al. |
| 5,960,792 A | 10/1999 | Lloyd et al. |
| 5,989,245 A | 11/1999 | Prescott |
| 6,001,069 A | 12/1999 | Tachibana et al. |
| 6,014,970 A | 1/2000 | Irvi et al. |
| 6,024,718 A | 2/2000 | Chen et al. |
| 6,026,808 A | 2/2000 | Armer et al. |
| 6,027,495 A | 2/2000 | Miller |
| 6,041,253 A | 3/2000 | Kost et al. |
| 6,061,597 A | 5/2000 | Rieman et al. |
| 6,076,519 A | 6/2000 | Johnson |
| 6,083,159 A | 7/2000 | Driscoll, Jr. et al. |
| 6,095,141 A | 8/2000 | Armer et al. |
| 6,098,620 A | 8/2000 | Lloyd et al. |
| 6,102,298 A | 8/2000 | Bush et al. |
| 6,106,547 A | 8/2000 | Huei-Jung |
| 6,113,558 A | 9/2000 | Rosenschein et al. |
| 6,113,570 A | 9/2000 | Siegel et al. |
| RE36,939 E | 10/2000 | Tachibana et al. |
| 6,158,388 A | 12/2000 | Wenstrand |
| 6,158,431 A | 12/2000 | Poole |
| 6,161,536 A | 12/2000 | Redmon et al. |
| 6,176,839 B1 | 1/2001 | DeLuis et al. |
| 6,186,963 B1 | 2/2001 | Schwarze et al. |
| 6,190,315 B1 | 2/2001 | Kost et al. |
| 6,190,336 B1 | 2/2001 | Duarte et al. |
| 6,206,842 B1 | 3/2001 | Tu et al. |

| | | |
|---|---|---|
| 6,206,843 B1 | 3/2001 | Iger et al. |
| 6,231,528 B1 | 5/2001 | Kaufman et al. |
| 6,234,990 B1 | 5/2001 | Rowe et al. |
| 6,251,099 B1 | 6/2001 | Kollias et al. |
| 6,254,294 B1 | 7/2001 | Muhar |
| 6,273,864 B1 | 8/2001 | Duarte et al. |
| 6,311,573 B1 | 11/2001 | Bhardwaj |
| 6,321,109 B2 | 11/2001 | Ben-Haim et al. |
| 6,322,527 B1 | 11/2001 | Talish |
| 6,325,769 B1 | 12/2001 | Klopotek |
| 6,450,417 B1 | 9/2002 | Gipson et al. |
| 6,478,754 B1 | 11/2002 | Babaev |
| 6,500,133 B2 | 12/2002 | Martin et al. |
| 6,533,484 B1 * | 3/2003 | Osei et al. .................. 401/205 |
| 6,533,803 B2 | 3/2003 | Babaev |
| 6,569,099 B1 * | 5/2003 | Babaev ....................... 600/439 |
| 6,583,071 B1 | 6/2003 | Weidman et al. |
| 6,601,581 B1 | 8/2003 | Babaev |
| 6,623,444 B2 | 9/2003 | Babaev |
| 6,659,365 B2 | 12/2003 | Gipson et al. |
| 6,663,554 B2 | 12/2003 | Babaev |
| 6,666,431 B2 | 12/2003 | McCusker |
| 6,723,064 B2 | 4/2004 | Babaev |
| 6,732,744 B2 | 5/2004 | Olshavsky et al. |
| 6,761,729 B2 | 7/2004 | Babaev |
| 6,916,296 B2 | 7/2005 | Soring et al. |
| 6,960,173 B2 | 11/2005 | Babaev |
| 6,964,647 B1 | 11/2005 | Babaev |
| 7,316,664 B2 | 1/2008 | Kadziauskas et al. |
| 2002/0080206 A1 | 6/2002 | Lin |
| 2002/0177846 A1 | 11/2002 | Mulier et al. |
| 2003/0195644 A1 | 10/2003 | Borders et al. |
| 2003/0236560 A1 | 12/2003 | Babaev |
| 2004/0028552 A1 | 2/2004 | Bhardwaj et al. |
| 2004/0030254 A1 | 2/2004 | Babaev |
| 2004/0034982 A1 | 2/2004 | Wieber et al. |
| 2004/0055376 A1 | 3/2004 | Thompson et al. |
| 2004/0073175 A1 * | 4/2004 | Jacobson et al. ............ 604/251 |
| 2004/0186384 A1 | 9/2004 | Babaev |
| 2006/0025716 A1 | 2/2006 | Babaev |
| 2006/0058710 A1 | 3/2006 | Babaev |

FOREIGN PATENT DOCUMENTS

| | | |
|---|---|---|
| EP | 0 437 155 B1 | 2/1990 |
| EP | 416106 | 3/1991 |
| EP | 0 657 226 B1 | 11/1994 |
| GB | 2 099 710 A | 12/1982 |
| GB | 2 101 500 A | 1/1983 |
| JP | 2000237275 A2 | 9/2000 |
| RU | 1106485 | 10/1982 |
| RU | 1827239 | 5/1990 |
| SU | 1106485 A | 10/1982 |
| WO | WO 96/35383 | 11/1996 |
| WO | 97/17933 | 5/1997 |
| WO | WO-2002/024150 | 3/2002 |
| WO | WO-02/28350 | 4/2002 |

OTHER PUBLICATIONS

U.S. Appl. No. 90/007,613, filed Jul. 5, 2005, Babaev.
Journal of Burn Care & Rehabilitation; vol. 21, No. 4; Jul./Aug. 2000 pp. 333-338.
Design and Application of Low-Frequency Ultrasound and Its Combination With Laser Radiation in Surgery and Therapy—Critical Reviews in Biomedical Engineering; 2001; pp. 502-519.
"Comparison Possibilities . . . " Zharov et al., Biomedical Optoacoustics, Proceedings of SPIE, vol. 3916 (2000), pp. 331-339.
European Search Repost corresponding to EPO Appl. No. 01973544.8-2107-US0130096.
XP002294548, Abstract corresponding to SU 914099.
Department of Health & Human Services Letter dated Jun. 25, 2004 (3 pages).
Department of Health & Human Services Letter dated May 17, 2005 (3 pages).
Image File Wrapper for U.S. Appl. No. 11/473,934, filed Jun. 23, 2006.

* cited by examiner

REMOVABLE APPLICATOR NOZZLE FOR ULTRASOUND WOUND THERAPY DEVICE

PRIORITY

This application hereby claims priority to U.S. Provisional Patent Application Ser. No. 60/693,560 titled "REMOVABLE APPLICATOR NOZZLE FOR ULTRASOUND WOUND THERAPY DEVICE," filed on Jun. 23, 2005, the entire contents of which are incorporated herein by reference.

BACKGROUND

Ultrasound waves have been widely used in medical applications, including both diagnostics and therapy as well as many industrial applications. One diagnostic use of ultrasound waves includes using ultrasonic waves to detect underlying structures in an object or a human tissue. In this procedure, an ultrasonic transducer is placed in contact with the object or tissue via a coupling medium and high frequency (1-10 MHz) ultrasonic waves are directed into the tissue. Upon contact with various underlying structures, the waves are reflected back to a receiver adjacent the transducer. By comparison of the signals of the ultrasonic wave as sent with the reflected ultrasonic wave as received, an image of the underlying structure can be produced. This technique is particularly useful for identifying boundaries between components of tissue and can be used to detect irregular masses, tumors, and the like.

Two therapeutic medical uses of ultrasound waves include aerosol mist production and contact physiotherapy. Aerosol mist production makes use of a nebulizer or inhaler to produce an aerosol mist for creating a humid environment and delivering drugs to the lungs. Ultrasonic nebulizers operate by the passage of ultrasonic waves of sufficient intensity through a liquid, the waves being directed at an air-liquid interface of the liquid at a point underneath or within the liquid. Liquid particles are ejected from the surface of the liquid into the surrounding air following the disintegration of capillary waves produced by the ultrasound. This technique can produce a very fine dense fog or mist. Aerosol mists produced by ultrasound are preferred over aerosol mists produced by other methods because a smaller particle size of aerosol can be obtained with the ultrasonic waves. One of the major shortcoming of inhalers and nebulizers is that the aerosol mist cannot be directed to a target area without an air stream, which decreases the efficiency of ultrasound.

Ultrasonic sprayers such as those sold by Sonic and Materials Inc., Misonix Inc., Sono-Tek Inc. (see, for example, U.S. Pat. Nos. 4,153,201, 4,655,393, and 5,516,043) operate by passing liquid through a central orifice of an ultrasound instrument-tip. Major disadvantages of these sprayers include non-uniform particle size, heating of liquid flow, and less efficiency of the ultrasound waves.

Contact physiotherapy applies ultrasonic waves directly to tissue in an attempt to produce a physical change in the tissue. In conventional ultrasound physiotherapy, an ultrasonic wave contacts the tissue via a coupling medium. Ultrasonic waves produced by the transducer travel through the coupling medium and into the tissue. The coupling medium is typically a bath of liquid, a jelly applied to the surface to be treated, or a water-filled balloon. Conventional techniques provide ultrasonic waves having an intensity of about 0.25 w/cm$^2$ to about 3 w/cm$^2$ at a frequency of about 0.8 to about 3 Megahertz. The treatment is applied to a skin surface for about 1 to about 30 minutes, for multiple times a week. The coupling medium can provide a cooling effect which dissipates some of the energy produced by the ultrasonic transducer.

More importantly, a coupling medium or direct contact between the tissue and ultrasonic transducer is desirable to transmit the ultrasonic waves from the to the skin surface because ambient air is a relatively poor medium for the propagation of ultrasonic waves.

Several beneficial effects have been reported from contact ultrasound physiotherapy, such as, for example, the following: local improvement of the blood circulation, heating of the tissue, accelerated enzyme activity, muscle relaxation, pain reduction, and enhancement of natural healing processes. Despite these beneficial effects, current techniques of medical physiotherapy using ultrasonic waves are limited by the desire of providing a direct contact interface between the ultrasonic transducer and the tissue to maintain an effective transmission of the ultrasonic waves from the transducer to the tissue.

The desire of direct contact with or without a coupling medium makes current methods undesirable. Some tissue conditions may be accessible to contact ultrasound devices but would be impractical for contact ultrasound treatment. For example, fresh or open wounds resulting from trauma, burns, surgical interventions are not suitable for direct contact ultrasound treatment because of the structural nature of the open wound and the painful condition associated with those wounds. Moreover, conventional contact ultrasound may have a destructive effect on these types of open wounds due to the close proximity of an oscillating tip of an ultrasonic transducer relative to the already damaged tissue surface.

Commonly-owned U.S. Pat. No. 6,569,099 discloses an ultrasonic device and method for wound treatment, the entire contents of which are incorporated herein by reference. This patent discloses, inter alia, a device that sprays liquid particles to a wound via an applicator. The liquid particles provide a medium for propagation of the ultrasonic waves.

As can be appreciated, an improved applicator may be desired to produce a more reliable and consistent flow of liquid particles to a wound bed or site.

SUMMARY

The present disclosure generally relates to the field of ultrasound wound therapy devices, and more particularly relates to a removable applicator nozzle for enabling a fluid to be sprayed towards a patient, thus providing a medium for ultrasonic waves to travel through and penetrate the tissue to a beneficial depth to provide bactericidal, therapeutic and other effects.

According to an aspect of the present disclosure, a removable applicator nozzle for use in treating a wound is provided. The removable applicator nozzle or applicator includes a nozzle, a valve and a cup. The nozzle includes a proximal portion, a distal opening and a valve interface. The proximal portion of the nozzle is engagable with a portion of an ultrasound wound therapy device. The distal opening of the nozzle allows at least a portion of a transducer tip of the ultrasound wound therapy device to pass therethrough. The valve interface defines an axis therethrough. The valve comprises a valve opening, an upper portion and a lower portion. The lower portion is engagable with the valve interface of the nozzle and the valve opening selectively allows fluid to flow therethrough. The cup includes an aperture which is engagable with at least the upper portion of the valve.

In use, fluid flows through the aperture of the cup, through the valve and onto at least a portion of the tip of the ultrasound wound therapy device. The fluid drips from the nozzle to a top surface of the transducer tip, drips/wraps around the transducer tip and then a vacuum effect takes place which moves the fluid forward to a distal end of the transducer tip.

It is envisioned for the fluid to drip onto a portion of the ultrasound wound therapy device that is proximal to the distal-most portion of the tip of the ultrasound wound therapy device. It is also envisioned for the fluid to drip on or about the most distal-most portion of the tip of the ultrasound wound therapy device.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF VARIOUS EMBODIMENTS

Embodiments of the presently disclosed removable applicator nozzle will now be described in detail with reference to the drawing figures wherein like reference numerals identify similar or identical elements. As used herein and as is traditional, the term "distal" refers to that portion which is farthest from the user while the term "proximal" refers to that portion which is closest to the user. Further, as used herein, the word "wound" refers to surface wounds, such as burns and skin lesions; internal wounds, such as ulcers and surgical cuts due to surgery; surgical incisions; injuries, including broken bones; and other conditions or applications requiring treatment using ultrasound wound therapy.

Figure 2:
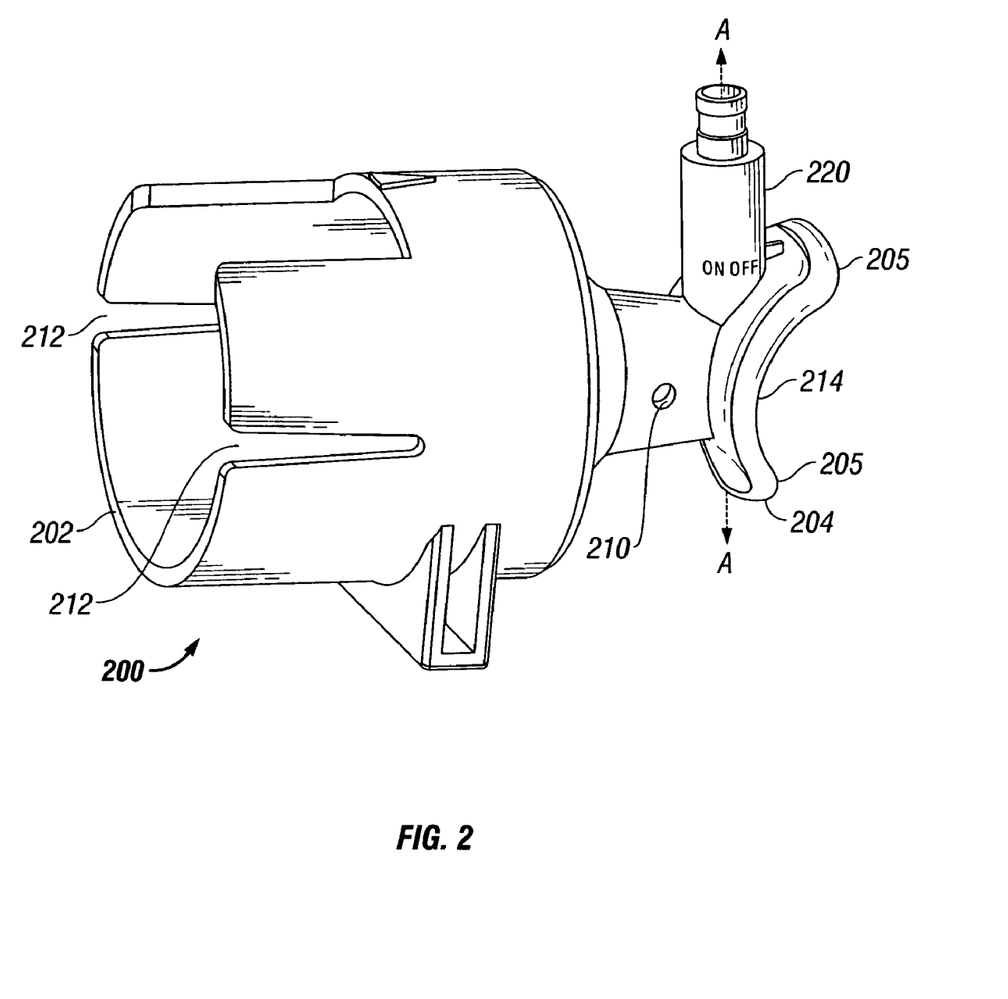
FIG. 2 is a perspective view of the removable applicator nozzle of FIG. 1.
Figure 3:
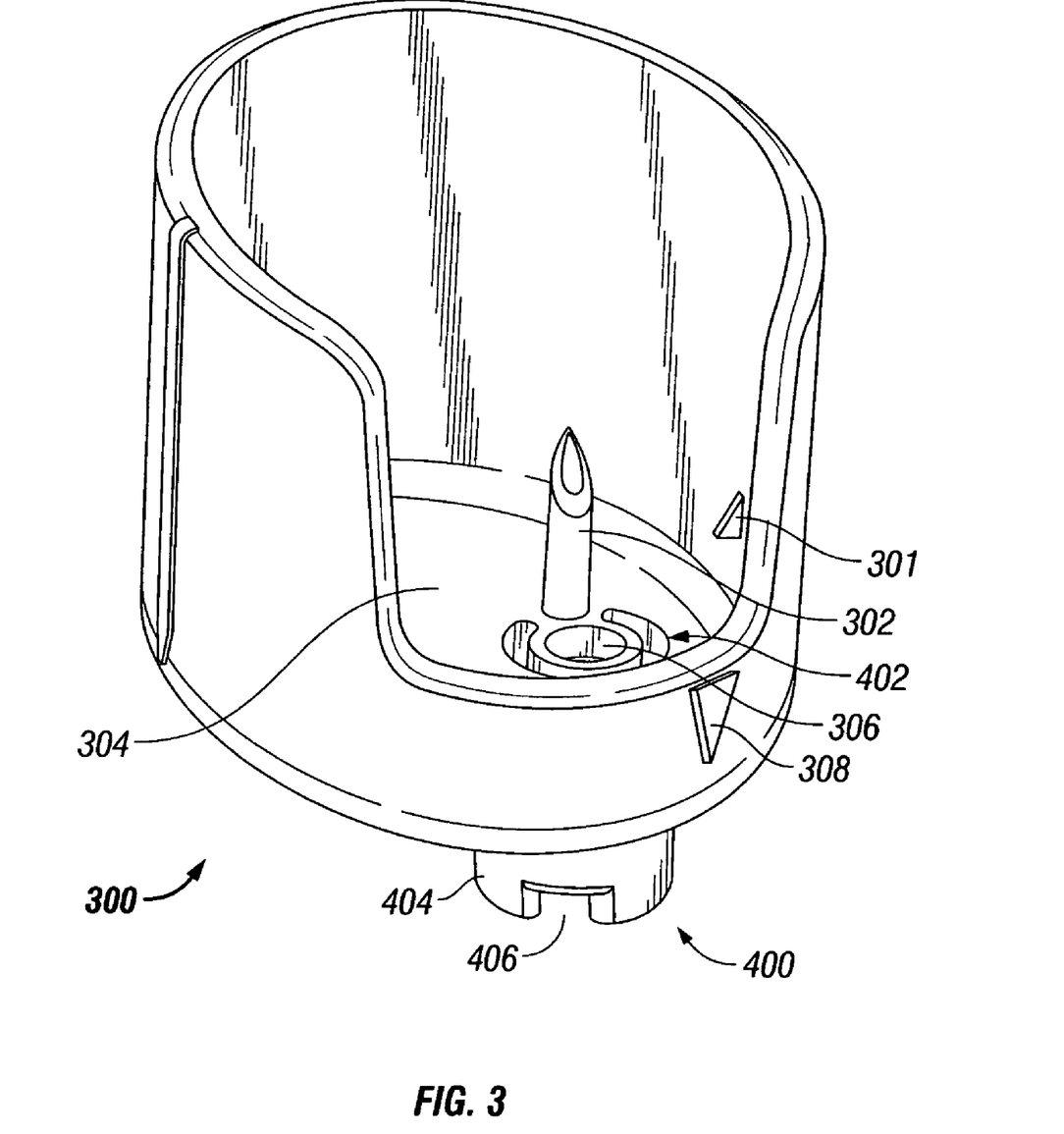
FIG. 3 is a perspective view of the cup and the valve of FIG. 1.

In the figures, a removable applicator nozzle or applicator according to an aspect of the present disclosure is generally designated as reference numeral 100. Applicator 100 generally includes a nozzle 200 (FIG. 2), a cup 300 (FIG. 3), and a valve 400 (FIG. 3). Referring to FIG. 2, the nozzle 200 includes a proximal portion 202, a distal portion 204, a plurality of alignment slots 212, a distal opening 214, and a valve interface 220 (also shown in FIG. 6). In an alternate embodiment, the applicator 100 includes a chip housing 230 (see FIGS. 4 and 5). The portion of the nozzle 200 that extends the farthest distally is distal tip 205.

It is envisioned for the applicator 100 in accordance with the present disclosure to be designed for use with an ultrasound wound therapy device, such as the device described in U.S. Pat. No. 6,569,099, the entire contents of which are incorporated herein by reference. The present disclosure is also related to U.S. Pat. Nos. 6,478,754 and 6,663,554 and U.S. patent application Ser. No. 09/684,044, the entire contents of both patents and the patent application are incorporated herein by reference.

Now referring to FIG. 3, the cup 300 includes a puncturing device 302, a lower portion 304 with an aperture 306 extending therethrough, and may include an alignment structure 308. The cup 300 may be designed to hold at least a portion of a bottle 600 (FIG. 1) therein. The bottle 600 generally holds a fluid 602, which may be saline. The cup 300 include structure, such as indent(s) 301, on the lower inside surface of the cup 300 as shown by FIG. 3 for enhancing the grip and fit of the bottle 600 within the cup 300. Indent(s) 301 are configured for damaging the bottle 600 upon removal of the bottle 600 from the cup 300, thereby preventing reuse of the bottle 600.

The valve 400 is also illustrated in FIG. 3. The valve 400 includes an upper portion 402, a lower portion 404 and a slot 406. The valve 400 selectively allows the fluid 602 from the bottle 600 to pass therethrough and towards the nozzle 200. It is envisioned for the valve 400 to be separate or removable from the applicator 100 for enabling removal of the valve from the applicator 100, in order for the valve 400 to be reused with other applicators 100 and for lowering production costs for the applicator 100.

Figure 1:
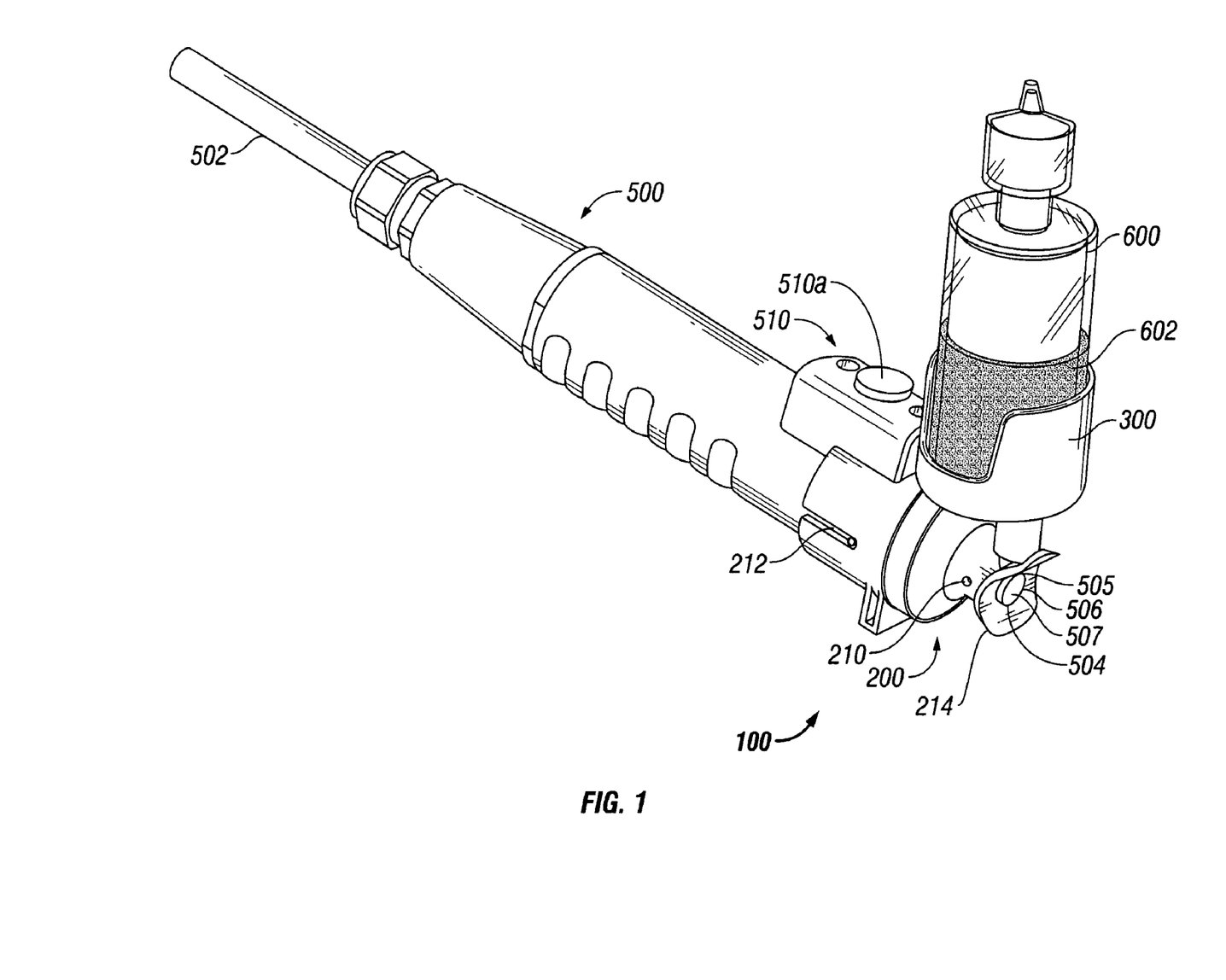
FIG. 1 is a perspective view of the removable applicator nozzle of the present disclosure including a nozzle, a cup and a valve, the removable applicator nozzle being illustrated operatively attached to a transducer of an ultrasound wound therapy device and with a bottle inserted therein.

Referring to FIGS. 1-3, the nozzle 200, the cup 300 and the valve 400 mechanically engage with one another to form the applicator 100. Specifically, the lower portion 404 of the valve 400 fits over the valve interface 220 of nozzle 200; the upper portion 402 of the valve 400 fits into the aperture 306 of the cup 300. When mechanically engaged, the cup 300 is capable of turning approximately 90° with respect to an axis A-A, as defined by the valve interface 220 (FIG. 2). Turning the cup 300 adjusts the valve 400 from a closed position where the fluid 602 cannot flow through, to an open position which provides a passage for the flow or the fluid 602. Turning the cup 300 back towards its original position closes the valve 400.

With specific reference to FIGS. 1, 4 and 5, the applicator 100 is mechanically connectable with an ultrasound wound therapy device 500, hereinafter referred to as a transducer assembly. When activated, the transducer assembly 500 produces ultrasonic waves having a frequency of about 1 kHz to about 10,000 MHz. The ultrasonic waves deliver ultrasonic energy to a wound surface, including below the wound surface, via a spray which acts as the coupling agent for the ultrasonic energy as further described below. The ultrasonic energy provides bactericidal, therapeutic and other effects for decreasing the healing time for the wound as disclosed by U.S. Pat. No. 6,569,099, the entire contents of which are incorporated herein by reference.

Specifically, the proximal portion 202 of the nozzle 200 slides over a distal portion 504 of the transducer assembly 500. The plurality of aligning slots 212 (illustrated as two slots) of the nozzle 200 engage with a plurality of aligning pins 508 (FIG. 4) of the transducer assembly 500. When connected, the distal end 506 of a tip 505 of the transducer assembly 500 may extend distally of the distal opening 214 of the nozzle 200 but not to a location that is distal of the tip 205 of the nozzle 200. That is, when the transducer assembly 500 is inserted through the applicator 100, the distal end 504 of the transducer assembly 500 extends between the distal opening 214 and the distal tip 205 of the nozzle 200, such that the distal dip 205 of the nozzle 200 is coaxially disposed about the distal end 504 of the transducer assembly 500.

In use, the cup 300 is inserted onto the "valve" 400 (as shown in FIG. 3) and the valve 400 is inserted onto the valve interface 220 of the nozzle 200. The transducer assembly 500 is then aligned and coupled with the nozzle 200, via aligning slots 212 and alignment pins 508. The distal end 506 of the transducer assembly 500 is inserted through the proximal portion 202 of the nozzle 200, continues through the distal portion 204 of the nozzle 200, and out through the distal opening 214 of the nozzle 200. The bottle 600 may then be placed into the cup 300. Upon insertion of the bottle 600 into the cup 300, the puncturing device 302 of the cup 300 punctures a hole in the bottle 600. The alignment structure 308 may assist the user in properly positioning the bottle 600 in the cup 300. It is envisioned for the bottle 600 to be inserted into the cup 300 prior to the applicator 100 being coupled with the transducer assembly 500. The insertion of the cup 300 and valve 400 into the nozzle 200, the coupling of the applicator 100 and the transducer assembly 500, and the insertion of the bottle 600 into the cup 300 allow the applicator 100 to be utilized vis-à-vis the transducer assembly 500.

To utilize the applicator 100 with the transducer assembly 500, a user turns the cup 300 approximately 90°. The turning of the cup 300 "opens" the "valve" 400 by aligning a valve opening 222 (FIG. 6) with the hole in the nozzle 200 and allows the fluid 602 to pass through the valve 400. The nozzle 200 is specifically designed such that the fluid 602 drips through the valve interface 220 of the nozzle 200 and onto a portion of the tip 505 of the transducer assembly 500. The fluid 602 drips onto a portion of the tip 505 that is proximal the location of the distal end 506 of the tip 505 of the transducer assembly 500.

In a particularly useful embodiment, the valve opening 222 (FIG. 6) is appropriately sized to allow a desired amount of fluid 602 to pass therethrough such that the fluid 602 that drips onto the tip 505 of the transducer assembly 500 can wrap around the circumference of the tip 505. Such an effect is known as the Babaev effect, or vacuum effect, and creates a capillary action that wicks or applies the fluid 602 around the circumference of the tip 505 of the transducer assembly 500.

It is envisioned for the diameter of the valve opening 222 to be in the range of about 0.027 inches to about 0.037 inches and may be in the more specific range of about 0.031 inches to about 0.033 inches. Additionally, this size valve opening 222 may generate relatively uniform particle sizes of fluid 602. These particle sizes may be approximately equal to 60 µm in diameter. It is also envisioned for the fluid 602 to drip onto a front face 507 of the tip 505 of the transducer assembly 500, as shown by FIG. 4a of U.S. Pat. No. 6,569,099.

A user may then wait for approximately three seconds for the fluid 602 to coat the circumference of the tip 505 of the transducer assembly 500 before he activates the transducer assembly 500. To activate the transducer assembly 500, the user engages the switch 510. Two switches 510a, 510b are depicted in the figures (FIG. 1; and FIGS. 4 and 5, respectively) and other types of switches 510 are also envisioned and are within the scope of the present disclosure. Upon activation of the switch 510, the tip 505 of the transducer assembly 500 is displaced between about 60 µm to about 70 µm as the tip 505 vibrates at a rate of about 1 kHz to about 10,000 MHz.

Such a displacement provides the energy levels needed to provide therapeutic benefit and may minimize the aerosolization of bacteria and/or other tissue exudates. The displacement of the tip 505 causes a vacuum effect between the tip 505 of the transducer assembly 500 and the distal opening 214 of the nozzle 200, which moves the fluid 602 from the circumference of the tip 505 distally out through the distal opening 214 of the nozzle 200. Upon exiting the applicator 100, the fluid 602 is in the form of a mist. Such a fluid mist medium ameliorates the dissipation effect that ultrasonic energy typically undergoes as ultrasonic waves travel in air.

The separation distance between the free end surface of the transducer tip 505 and the surface or object to be sprayed should be a non-contact distance of at least 0.1 inches (2.5 mm). Preferably, the separation distance is from about 2.5 mm to about 51 cm, more preferably, from about 15 mm to about 25 mm. The fluid 602 to be sprayed and provided within the bottle 600 can be any appropriate carrier, such as saline, water (regular or distilled), or oil to be applied to tissue, such as a vegetable, peanut, or canola oil, optionally with a soluble pharmaceutical (e.g., an antibiotic), antiseptic, conditioner, surfactant, emollient, or other active ingredient. The fluid 602 can also be a combination of two or more fluids and/or substances having microscopic particles, such as powder and the like.

As can be appreciated, the apparatus as described enables a gravity feed system for delivery of the fluid 602 to the transducer assembly 500. Such a system may not pressurize the fluid 602. Pressurization of the fluid 602 may create inconsistent particle size and/or velocity, which may create aerosolization.

It is envisioned for the bottle 600 of the present disclosure to be eliminated and/or replaced with another structure for delivering the fluid 602 to the transducer assembly 500, such as a fluid bag (not shown). In such an embodiment, it is envisioned for the fluid 602 to be delivered to the transducer assembly 500 in a pressurized state. Desirably, the pressurized fluid 602 in such an embodiment may be approximately equal to the pressure of the fluid 602 exiting the bottle 600, as in the previous embodiment. This pressure may be relatively small and may be dictated by the pressure associated with gravity and the size opening of the valve opening 222. This type of arrangement, using a fluid bag as opposed to a bottle 600, may be useful in situations where the bottle 600 may interfere with accessing a particular site. It may also be useful to use a fluid bag in situations where the transducer assembly 500 is held in a general vertical orientation and/or to allow for a greater amount of fluid to be used (i.e., a fluid bag may be able to hold more fluid 602 than the bottle 600). Moreover, when the bottle 600 is replaced with a fluid bag (or another suitable replacement), the cup 300 may not be necessary.

It is envisioned for a plurality of valve openings 222 to be included in the applicator 100. A plurality of valve openings 222 may be particularly useful to allow the tip 505 of the transducer assembly 500 to be evenly coated with fluid 602, especially when the transducer assembly 500 is orientated in a generally vertical direction.

It is envisioned for the applicator 100 to include an aligning structure (not shown) for creating a uniform gap between the tip 505 of the transducer assembly 500 and the distal opening 214 of the nozzle 200. This uniform gap may be in the range of about 10 mm to about 20 mm with 18 mm currently being used and may further ensure a proper vacuum effect between the tip 505 of the transducer assembly 500 and the distal opening 214 of the nozzle 200.

Figure 4:
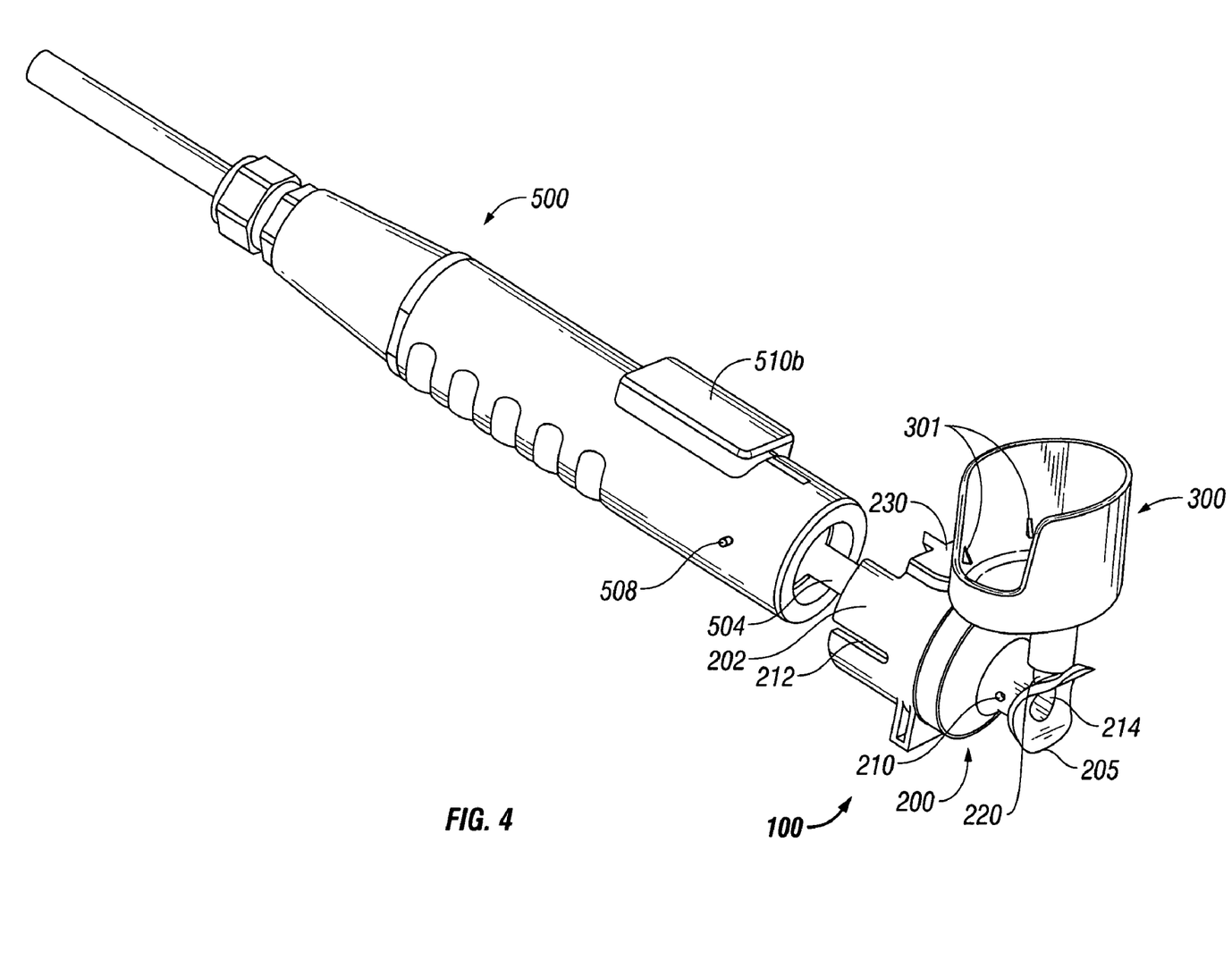
FIG. 4 is a perspective view of a removable applicator nozzle of an alternate embodiment partially inserted into a transducer of an ultrasound wound therapy device.
Figure 5:
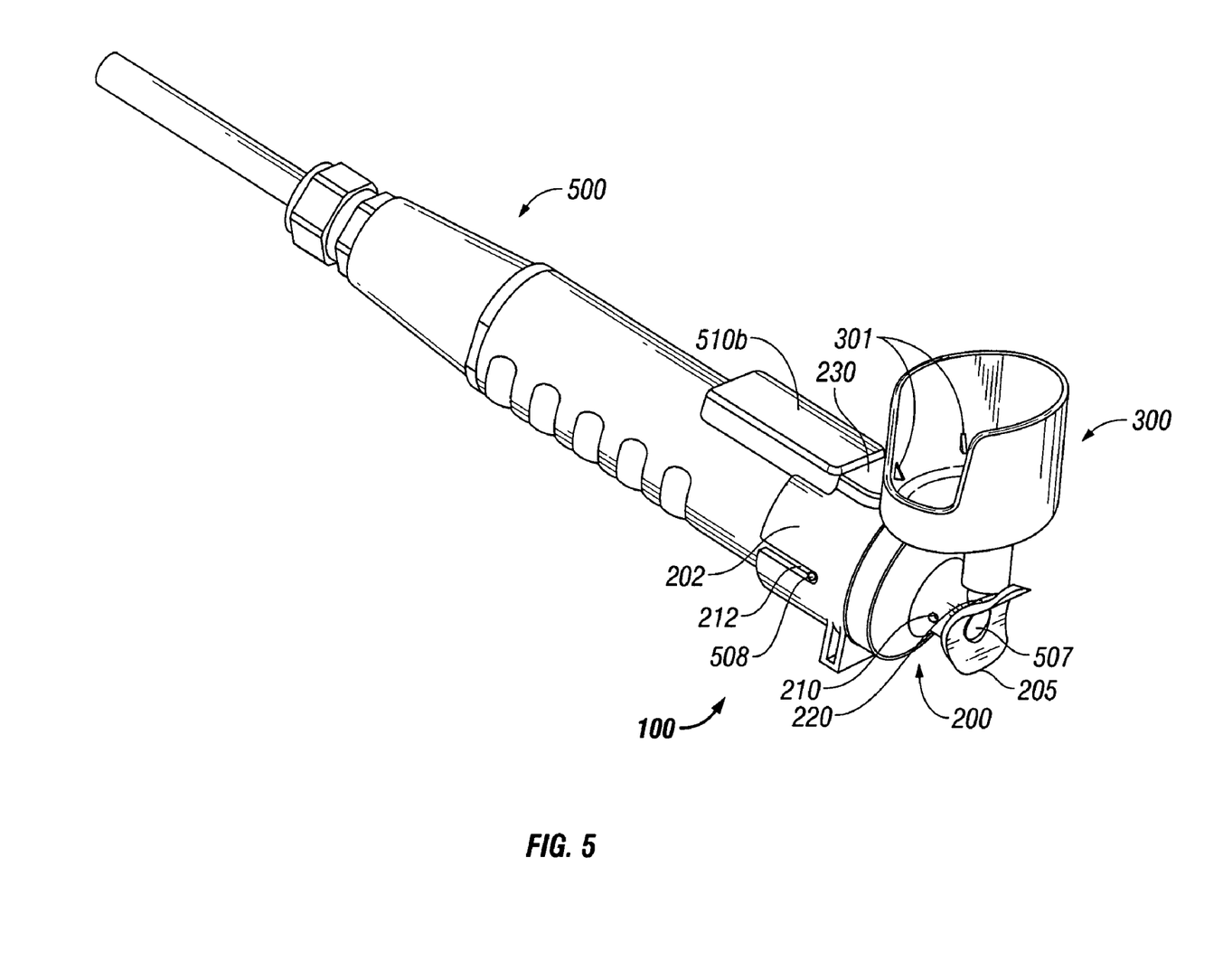
FIG. 5 is a perspective view of the removable applicator nozzle of FIG. 4 illustrated fully inserted into the transducer of FIG. 4.
Figure 6:
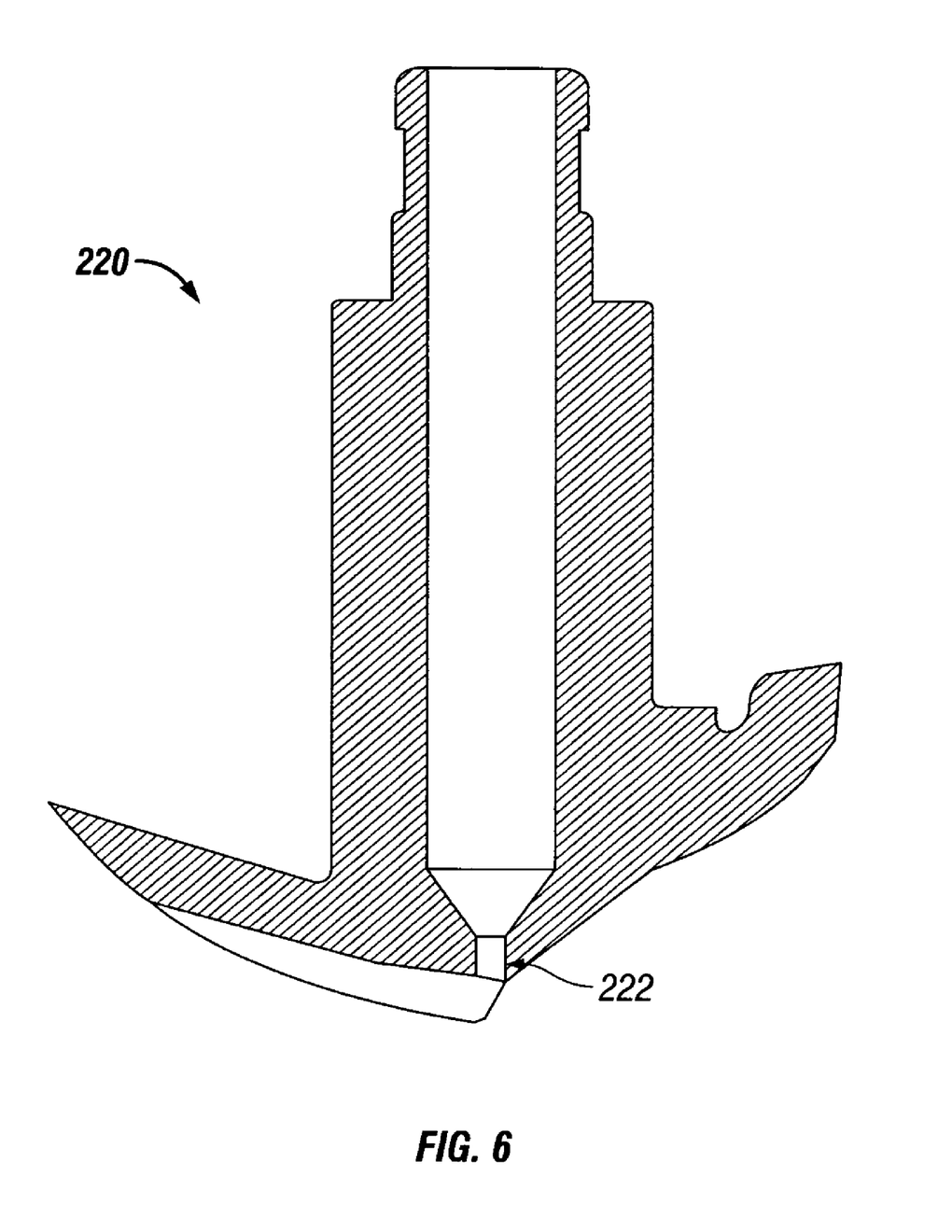
FIG. 6 is a cross-sectional view a valve interface of the removable applicator nozzle of FIGS. 2 and 4.

As shown in FIGS. 4 and 5, the alternate embodiment of the applicator 100 includes a chip housing 230. The chip housing 230 is keyed to interlock with the switch 510b of the transducer. A IC chip (not shown) is housed within the chip housing 230 and may be programmed to limit the number of times the applicator 100 is attached to the transducer assembly 500. Specifically, the IC chip may only allow the applicator 100 to be used one time and/or for a limited amount of time. This feature could help ensure that the applicator 100 is used, e.g., only once, thus preventing potential non-sterile use and/or possible cross-contamination, if used/maintained improperly.

In operation, the IC chip keeps count of the number of times the applicator 100 is attached to the transducer assembly 500. After the applicator 100 has been attached more than a predetermined number of times, e.g., five times, the IC chip transmits a signal to activate a solenoid or other device (software as well and is the current method being considered) for positioning a blocker to prevent the applicator 100 from being re-attached to the transducer assembly 500. The signal is transmitted after the applicator 100 is removed from the transducer assembly 500. Other functions of the chip are also envisioned and are within the scope of the present disclosure.

The IC chip includes a power source, such as a battery, for powering the IC chip and/or the solenoid. The IC chip can be an ASIC and/or a combination of components, such as timing circuitry; memory for storing data and the number of times the applicator 100 has been attached to the transducer assembly 500; battery; solenoid; control circuitry for activating the solenoid; and a blocker in operative communication with the solenoid.

In order to count the number of times the applicator 100 is attached to the transducer assembly 500, the IC chip includes a toggle switch which is toggled every time the applicator 100 is attached to the transducer assembly 500. The toggling of the toggle switch is sensed by the IC chip and causes the IC chip to increase its count by one. If the count exceeds the predetermined number stored by the IC chip, following removal of the applicator 100, the IC chip transmits the signal for activating the solenoid or software as described above.

It is envisioned for the applicator 100 to include an LCD or other display for displaying the number of times the applicator 100 has been attached to the transducer assembly 500. A sterilization icon can also be displayed by the LCD or other display. The sterilization icon is selected from a group of pre-stored sterilization icons for informing the user that sterilization of the applicator 100 is not required, recommended or required.

A message can also be displayed by the LCD or other display after a single use (or multiple uses) of the applicator 100. The message can state that additional use of the applicator 100 is not allowed or recommended and to replace the applicator 100 with another applicator 100.

It is also envisioned for the switch 510 on the transducer assembly 500 to be able to simultaneously open/close the valve 400 and activate/deactivate the transducer assembly 500. Such a switch 510 would allow a user to effectively utilize the transducer assembly 500/applicator 100 in a singe motion (i.e., the user would not first have to turn the cup 300 and then activate the switch 510 of the transducer assembly 500). Use of a solenoid valve (not shown) is envisioned to accomplish such utilization of the transducer assembly 500/applicator 100.

It is further envisioned for a plurality of vent holes 210 (FIG. 2) to be disposed on the nozzle 200. The vent holes 210 would help provide a pressure relationship for the fluid and may help provide the vacuum effect. It is also envisioned for the bottle 600 to include a plurality of vent holes (not shown).

As illustrated in FIGS. 1, 3, 4 and 5, the distal portion 204 of the nozzle 200 may be curved and/or contoured to focus ultrasonic energy as well as to complement standing wave potential. A similar characteristic is described in U.S. patent application Ser. No. 09/774,145, the entire contents of which are incorporated herein by reference. This shape may also limit inadvertent contact between the transducer tip 505 and a patient and/or a user of the transducer assembly 500.

It is further envisioned that the applicator 100 is able to ionize fluid (saline) particles as the particles are atomized off a face of the transducer assembly 500 to support cell stimulation.

The applicator 100 or ultrasound wound therapy device 500 can be provided with a laser or ultrasonic transducer for measuring the non-contact distance or stand-off distance from a wound surface. A feedback control mechanism can also be provided for indicating whether the measured non-contact distance is suitable for effecting optimum beneficial bactericidal, therapeutic and/or other effects. The feedback assembly is integrated with the transducer assembly and corresponding electronics housed within an ultrasonic generator for obtaining the measured non-contact distance data and processes the data to determine whether the measured non-contact distance is optimum for treatment purposes.

If the non-contact distance is determined not to be the optimum non-contact distance, the feedback control mechanism can sound an audible alarm or display a message on a display, such as the LCD display of the applicator 100. The alarm or message can indicate if the non-contact distance should be decreased or increased. If the applicator 100/ultrasound wound therapy device 500 is mounted to a robotic arm, the feedback control mechanism can in turn control the robotic arm for increasing or decreasing the non-contact distance.

It is to be understood that the foregoing description is merely a disclosure of particular embodiments and is in no way intended to limit the scope of the disclosure. Other possible modifications will be apparent to those skilled in the art and all modifications will be apparent to those in the art and all modifications are to be defined by the following claims.

What is claimed is:

1. A method for promoting wound healing comprising the steps of:
    providing a transducer which emits ultrasonic energy;
    providing an applicator, comprising:
        a nozzle including a proximal portion, a distal opening and a valve interface, the proximal portion being engageable with a portion of an ultrasound wound therapy device, the distal opening allowing at last a portion of a transducer tip of the ultrasound wound therapy device to pass therethrough;
        a valve comprising a valve opening, an upper portion and a lower portion, the upper and lower portion being rotatable with respect to each other, the lower portion being selectively engageable with the valve interface of the nozzle, the upper portion being in fluid communication with a fluid source, and the valve opening selectively allowing fluid to flow therethrough; and
        a cup including an aperture, the aperture in fluid communication with at least the upper portion of the valve;
    activating the transducer to emit ultrasonic energy; and
    turning the cup to selectively allow fluid to flow from the fluid source through the valve opening towards a portion of the transducer;
    wherein, following activation of the transducer and contact of said portion of the transducer with said fluid a spray is generated, and wherein the emitted ultrasonic energy is delivered to the wound through the spray to decrease the healing time of the wound.

2. The method according to claim 1, wherein when the transducer is activated, the transducer tip vibrates at a rate of about 1 kHz to about 10,000 MHz.

3. The method of claim 1, wherein the fluid is saline.

4. The method of claim 1, wherein the emitted ultrasonic energy is delivered to the wound through the spray from a non-contact distance of at least 0.1 inches between the transducer and the wound.

5. The method of claim 1, wherein the fluid source is a fluid bag.

6. The method of claim 1, wherein the fluid source is a bottle containing saline.

7. The method of claim 1, wherein the ultrasonic energy penetrates the tissue to a beneficial depth to provide bactericidal and/or other therapeutic effects.

8. The method of claim 1, wherein the fluid source is a bottle containing saline, and wherein the bottle is inserted on the cup.

9. The method of claim 1, wherein the step of turning the cup to selectively allow fluid to flow from the fluid source through the valve opening towards a portion of the transducer is performed prior to the step of activating the transducer to emit ultrasonic energy.

10. The method of claim 1, wherein the valve opening has a diameter in the range of about 0.027 inches to about 0.037 inches.

11. The method of claim 1, wherein one or more vent holes are disposed on the nozzle.

12. The method of claim 1, wherein the cup contains a single puncturing device.

13. The method of claim 3, wherein the ultrasonic energy penetrates the tissue to a beneficial depth to provide bactericidal and/or other therapeutic effects.

14. The method of claim 4, wherein the ultrasonic energy penetrates the tissue to a beneficial depth to provide bactericidal and/or other therapeutic effects.

15. The method of claim 9, wherein the valve opening has a diameter in the range of about 0.027 inches to about 0.037 inches.

16. The method of claim 10, wherein the valve opening has a diameter in the range of about 0.031 inches to about 0.033 inches.

17. The method of claim 15, wherein the valve opening has a diameter in the range of about 0.031 inches to about 0.033 inches.

* * * * *